(12) United States Patent
Beebe

(10) Patent No.: US 8,343,444 B2
(45) Date of Patent: Jan. 1, 2013

(54) DEVICE FOR IMPROVED CELL STAINING AND IMAGING

(75) Inventor: David J. Beebe, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1039 days.

(21) Appl. No.: 11/591,335

(22) Filed: Nov. 1, 2006

(65) Prior Publication Data

US 2008/0101997 A1    May 1, 2008

(51) Int. Cl.
*A61B 10/00* (2006.01)
(52) U.S. Cl. .......... 422/536; 422/50; 422/500; 422/502; 422/504; 422/82.05; 422/421
(58) Field of Classification Search .................. 422/102, 422/82.05, 50, 421, 500, 502, 504, 536
See application file for complete search history.

(56) References Cited

U.S. PATENT DOCUMENTS

| | | | |
|---|---|---|---|
| 6,989,927 B2 * | 1/2006 | Bonaventura | 359/391 |
| 2004/0055655 A1 * | 3/2004 | Beebe | 137/828 |
| 2005/0019231 A1 | 1/2005 | Kahl | |
| 2005/0079634 A1 * | 4/2005 | Wilding et al. | 436/514 |
| 2005/0266582 A1 * | 12/2005 | Modlin et al. | 436/164 |

OTHER PUBLICATIONS

Electron Microscopy Sciences. Web Archive. 16 pages. 2004.*

* cited by examiner

*Primary Examiner* — Jyoti Nagpaul
(74) *Attorney, Agent, or Firm* — Boyle Fredrickson, S.C.

(57) ABSTRACT

A device is provided for facilitating preparation of a sample for imaging. The device includes a cartridge having a generally flat, upper surface, a lower surface, an input port extending between the upper and lower surfaces thereof and an output port extending between the upper and lower surfaces thereof. The cartridge includes a first recess in the lower surface thereof having a first end communicating with the input port and a second end communicating with the output port. A cover slip has an upper surface engageable with the lower surface of the cartridge such that a portion of the upper surface of the cover slip communicates with the recess in the lower surface of the recess.

19 Claims, 3 Drawing Sheets

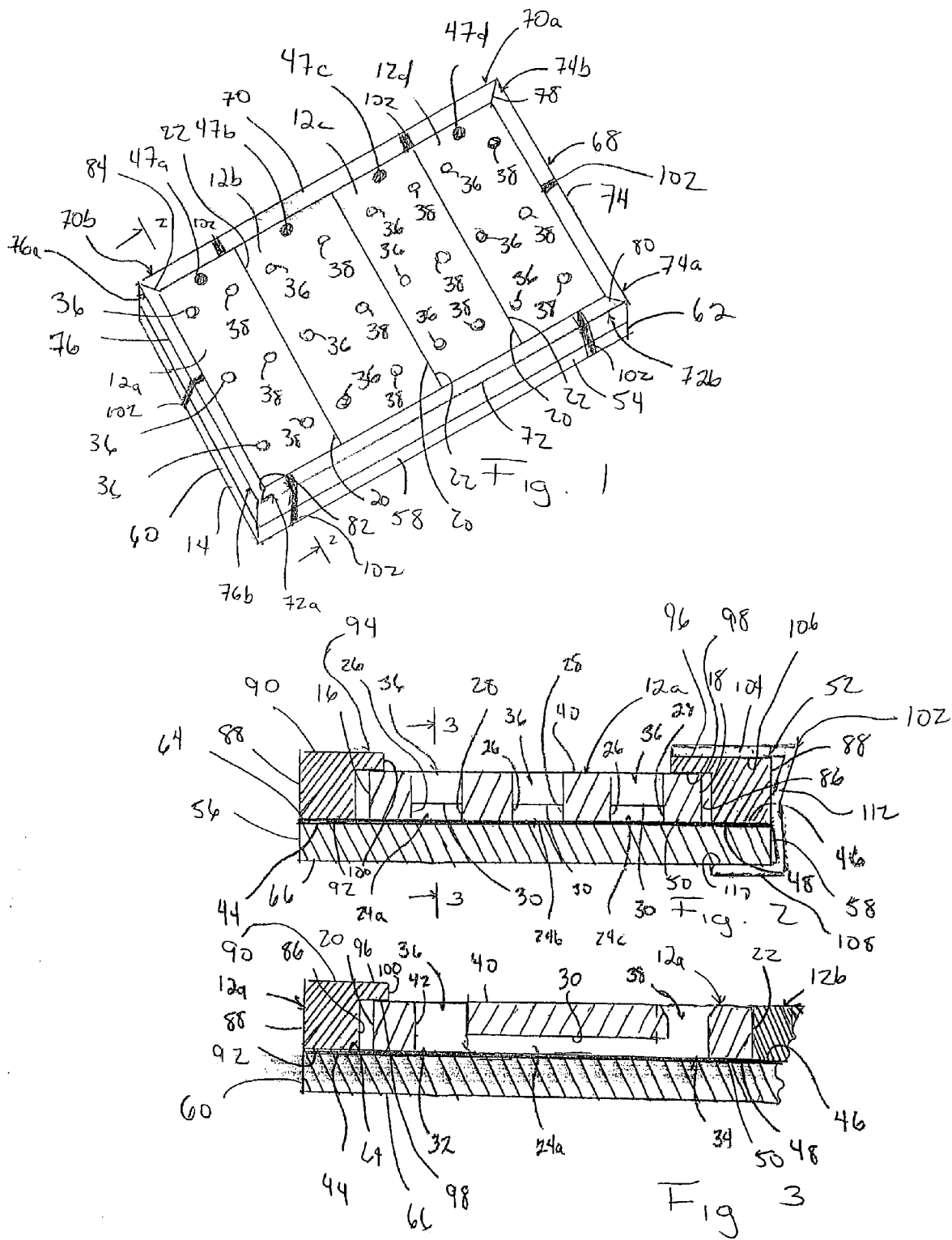

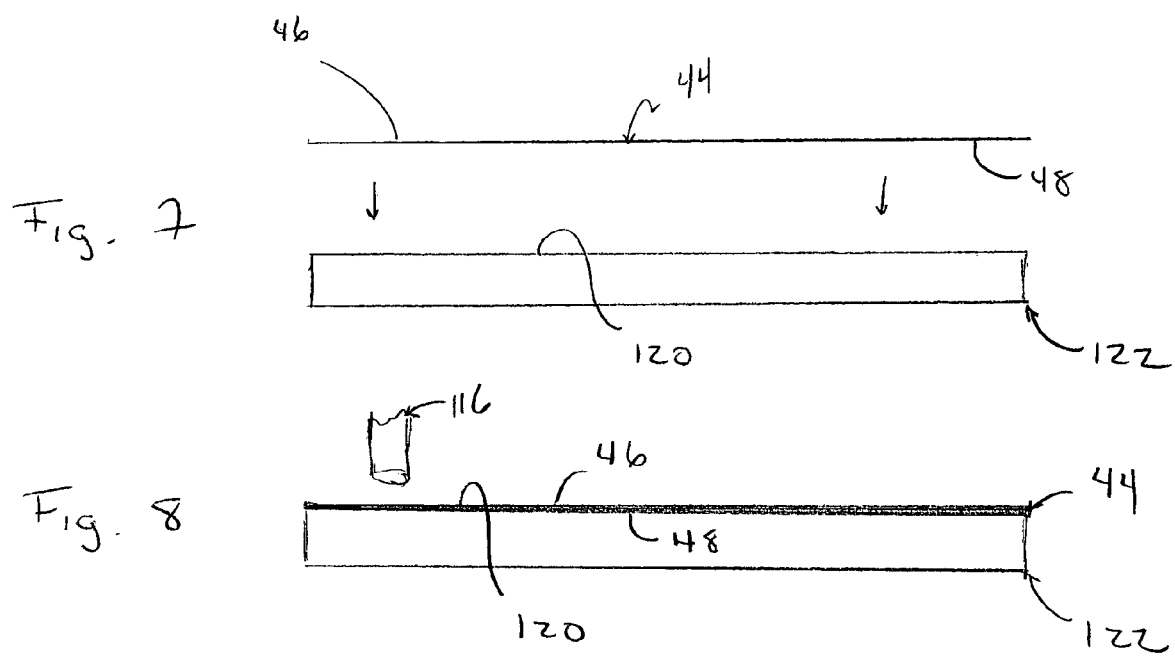

DEVICE FOR IMPROVED CELL STAINING AND IMAGING

REFERENCE TO GOVERNMENT GRANT

This invention was made with United States government support awarded by the following agency: NIH CA104162. The United States has certain rights in this invention.

FIELD OF THE INVENTION

This invention relates generally to microfluidic devices, and in particular, to a microfluidic device that facilitates the preparation of a sample for imaging.

BACKGROUND AND SUMMARY OF THE INVENTION

The preparation of a cover slip for cell imaging is a labor intensive operation. Typically, the preparation of the cover slip involves a number of steps for treating the cells for observation. These steps include fixating the cells to be observed for preservation and analysis. In addition, the cells are often mounted to the cover and/or immersed in a class-specific dye to enhance and highlight a specific portion of the cells for viewing. This process called "cell staining" often requires a substantial volume of dye. As is known, these dyes can be quite expensive. Once the cells have been stained according to the proper protocol, the dye must be removed or washed from the cells. Adequately washing the cells for observation may require the cells to be exposed to multiple washings. These washings can be time consuming. Given that current protocols for cell imaging contemplate a single treatment for each cover slip, it can be appreciated that even simple things like cell staining optimization require the processing of multiple cover slips.

Further, imaging multiple cover slips is a cumbersome process due to the time required to remove and replace a cover slip on a microscopic device. For example, the lens of the microscopic device must be cleaned between each use. In addition, locating the cell culture on the cover slip and properly focusing on the cells in order to provide good image contrast and high resolution may be time consuming. In view of the foregoing, it can be appreciated that it highly desirable to provide a device that reduces the time and cost associated with preparing a cover slip for cell imaging.

In order to overcome the limitations associated with preparation of a cover slip for cell imaging, various attempts have been made to develop a micro-channel system that incorporates a flow chamber that allows for the light-optical microscopic and light-spectroscopic examinations. By way of example, Kahl, United States Patent Application Publication No. US2005/0019231 A1 discloses a flow chamber made of plastic as an object carrier for light-microscopic examinations. The flow chamber includes at least one channel in a base plate. Inlet and outlet reservoirs communicate with opposite ends of the channel through an inlet and an outlet, respectively. A foil is arranged over the channel in the base plate and forms a bottom or cover for the channel. In order to make the flow chamber accessible to high-resolution microscopy, the foil is made from a relatively thin, highly transparent material. It is intended for the cells to be cultivated, fixated and stained with the channel. Thereafter, using an inverted microscope device, the cells in the channel can be observed.

While functional for its intended purpose, the flow chamber disclosed in the '231 application has certain inherent limitations. For example, the foil cannot be removed from the flow chamber and mounted on conventional cover slip. In addition, there is no mechanism for prevent leaks of fluid from the channel through the interface of the foil and the base plate. Further, the flow chamber disclosed in the '231 requires the foil to be affixed to by adhesion, hot pressing or laminating. This, in turn, increases the time associated with preparing the flow chamber for cell imaging.

Therefore, it is a primary object and feature of the present invention to provide a microfluidic device that facilitates the preparation of a sample for imaging.

It is a further object and feature of the present invention to provide a microfluidic device that facilitates the preparation of a sample for imaging that is simple and inexpensive to utilize.

It is a still further object and feature of the present invention to provide a microfluidic device that facilitates the preparation of a sample for imaging in a manner that is less time consuming than prior methods.

In accordance with the present invention, a device is proved for facilitating preparation of a sample for imaging. The device includes a cartridge having a generally flat, upper surface, a lower surface, an input port extending between the upper and lower surfaces thereof and an output port extending between the upper and lower surfaces thereof. The cartridge includes a first recess in the lower surface thereof having a first end communicating with the input port and a second end communicating with the output port. A cover slip has an upper surface engageable with the lower surface of the cartridge such that a portion of the upper surface of the cover slip communicates with the recess in the lower surface of the recess.

The device may also include a mounting structure removably connecting the cartridge to the cover slip. The mounting structure may include a substrate having an upper surface positionable against the lower surface of the cover slip and a lower surface. The substrate may includes a opening therethough for accommodating a microscopic device. The mounting structure may also include a bracket engageable with the cartridge on the substrate and a removable connector for interconnecting the bracket to the substrate and for maintaining the cartridge on the substrate. An adhesive may be provided for removably affixing the upper surface of the cover slip to the lower surface of the cartridge.

The cartridge and the cover slip may include fiduciary marks for facilitating the orientation of a microscopic device with respect thereto. In addition, the input port of the cartridge is defined by an input surface. At least a portion of the input surface is patterned to contain reagent droplets therein. It is contemplated for the outlet port in the cartridge has a generally funnel shaped cross section.

In accordance with a further aspect of the present invention, a device is provided for facilitating preparation of a sample for imaging. The device includes a cartridge having upper and lower surfaces and a first recess in the lower surface thereof. A cover slip has an upper surface engageable with the lower surface of the cartridge such that a first portion of the upper surface of the cover slip communicates with the first recess in the lower surface of the cartridge.

The lower surface of the cartridge includes a second recess therein and the upper surface of the cover slip has a second portion communicating with the second recess in the lower surface of the cartridge. The first and second recesses in the lower surface of the cartridge are generally parallel. The device may also include a substrate having an upper surface positionable against the lower surface of the cover slip and a lower surface. A removable connector is provided for maintaining the cartridge on the substrate.

The cartridge includes input and output ports. The input port is defined by a patterned input surface for containing reagent droplets therein and the outlet port has a generally funnel shaped cross section. The cartridge and the cover slip may include fiduciary marks In accordance with a still further aspect of the present invention, a device is provided for facilitating preparation of a sample for imaging. The device includes a cartridge having upper and lower surfaces and a plurality of generally parallel recesses forming in the lower surface thereof. Each recess has an input port at a first end thereof and an output port at a second end thereof. A cover slip has an upper surface engageable with the lower surface of the cartridge such that the upper surface of the cover slip and the plurality of recesses in the lower surface of the cartridge define a plurality of channels through the device.

A substrate has an upper surface positionable against the lower surface of the cover slip and a lower surface. A removable connector maintains the cartridge on the substrate. Each input port is defined by a patterned input surface for containing reagent droplets therein. Each outlet port has a generally funnel shaped cross section. The cartridge and the cover slip include fiduciary marks.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 1 is an isometric view of a device for facilitating the preparation of a sample for imaging;

FIG. 2 is a cross sectional view of the device of the present invention taken along line 2-2 of FIG. 1;

FIG. 3 is a cross sectional view of the device of the present invention taken along line 3-3 of FIG. 2;

FIG. 7 is an exploded, side elevational view the mounting of a cover slip on a conventional glass slide; and FIG. 8 is a side elevational view showing the cover slip mounted on the conventional glass slide.

DETAILED DESCRIPTION OF THE DRAWINGS

Figure 4:
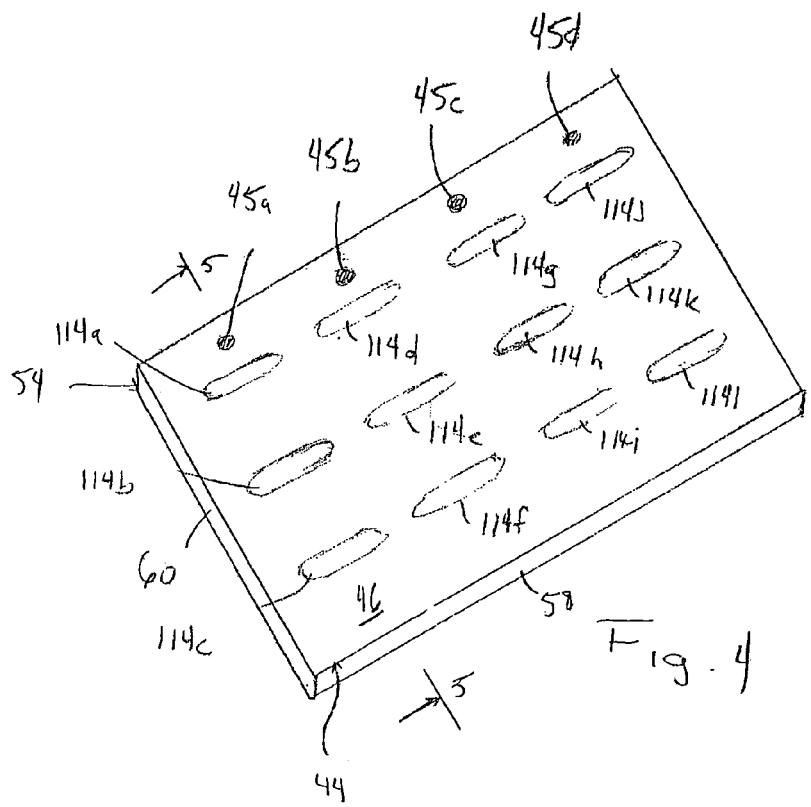
FIG. 4 is an isometric view of a substrate and cover slip for the device of the present invention.

Referring to FIGS. 1-3, a device for facilitating the preparation of a sample for imaging is generally designated by the reference numeral 10. Device 10 includes a plurality of microfluidic cartridges 12a-12d positioned adjacent each other on substrate 14. It can be appreciated that device 10 may include additional cartridges without deviating from the scope of the present invention. In addition, each cartridge 12a-12d is identical in structure. As such, the following description of cartridge 12a is understood to describe cartridges 12b-12d as if fully described hereinafter.

Cartridge 12a defined by first and second ends 16 and 18, respectively, and first and second sides 20 and 22, respectively. Channels 24a-24c are provided in cartridge 12a. It can be appreciated that the number and location of channels in cartridge 12a can vary without deviating from the scope of the present invention. Further, each channel 24a-24c is identical in structure. As such, the following description of channel 24a is understood to describe channels 24b-24c as if fully described herein.

Channel 24a extends along a longitudinal axis and is defines by first and second spaced sidewalls 26 and 28, respectively, and upper wall 30, FIGS. 2-3. Channel 24a further includes first and second ends 32 and 34, respectively, communicate with inlet 36 and outlet 38, respectively. Inlet 36 and outlet 38 communicate with upper surface 40 of cartridge 12a. It is completed for outlet 38 of channel 24a to have a generally funnel-shaped cross section to allow for robust and easy mating with a pipette (not shown). It is further contemplated for a portion of upper surface 40 of cartridge 12a about inlet 36 or for inner surface 42 defining inlet 36 to be physically or structurally patterned to contain fluid droplets within/adjacent inlet 36 and prevent cross channel contamination with the inlets of channels 24b-24c. Similarly, inlet 36 of channel 24a may have a generally funnel-shaped cross section to allow for robust and easy mating with a pipette (not shown). In addition, a portion of upper surface 40 of cartridge 12a about outlet 38 or the inner surface defining outlet 38 may be physically or structurally patterned to contain fluid droplets within/adjacent outlet 38 to prevent cross channel contamination.

Device 10 further includes cover slip 44 having upper and lower surfaces 46 and 48, respectively. Upper surface 46 of cover slip 44 is position against lower surface 50 of cartridge 12. Fiduciary marks 45a-45d and 47a-47d may be provided on cover slip 44, FIG. 4, and on corresponding cartridges 12a-12d (FIG. 1), respectively, to align cartridges on cover slip 44, for reasons hereinafter described. While it is contemplated to permanently bond upper surface 36 of cover slip 46 to lower surface 50 of cartridge 12, it also contemplated to allow for cover slip 44 to be removed from lower surface 50 of cartridge 12, for reasons hereinafter described. As best seen in FIGS. 2-3, with upper surface 46 of cover slip 44 positioned against lower surface 50 of cartridge 12, upper surface 46 of cover slip 44 partially defines and communicates with channels 24a-24c.

In order to prevent leakage and cross channel contamination between channels 24a-24c along upper surface 46 of cover slip 44, clamping frame 52 is provided. Clamping frame 52 includes substrate 54 defined first and second sides 56 and 58, respectively, and first and second ends 60 and 62, respectively. In the depicted embodiment, substrate 54 has a generally rectangular configuration. However, it can be appreciated that substrate can have other configurations without deviating from the scope of the present invention. Substrate 54 is further defined by upper and lower surfaces 64 and 66, respectively. Upper surface 64 of substrate 54 is adapted for receiving lower surface 48 of cover slip 44 thereon.

Clamping frame 52 further includes frame or bracket 68. In the depicted embodiment, bracket 68 has a generally frame-like configuration and is defined by first and second side elements 70 and 72, respectively, and first and second end elements 74 and 76, respectively. In order to assemble bracket 68, first end 70a of first side element 70 is joined to second end 74b of first end element 74 at corner 78; first end 74a of first end element 74 is joined to second end 72b of second side element 72 at corner 80; first end 72a of second side element 72 is joined to second end 76b of second end element 76 at corner 82; and first end 76a of second end element 76 is joined to second end 70b of first side element 70 at corner 84.

Bracket 68 further includes inner surface 86 and outer surface 88. Inner surface 86 of bracket 68 is defined by the inner surfaces of first and second side elements 70 and 72, respectively, and first and second end elements 74 and 76, respectively. Outer surface 88 of bracket 68 is defined by the outer surfaces of first and second side elements 70 and 72, respectively, and the outer surfaces of first and second end elements 74 and 76, respectively. Inner and outer surfaces 86 and 88, respectively, of bracket 68 are interconnected and spaced by upper and lower surfaces 90 and 92, respectively. Flange 94 projects radially inward from inner surface 86 of bracket 68 and is defined by upper surface 96 that is substantially flush with upper surface 90 of bracket 68 and lower surface 98 that extends from inner surface 86 of bracket 68. Upper and lower surfaces 96 and 98, respectively, of flange 94 are interconnected and spaced by inner edge 100.

In order to assemble device 10, lower surface 48 of cover slip 44 is received on upper surface 64 of substrate 54. Cartridges 12a-12d are positioned on upper surface 46 of cover slip 44 such that second side 22 of cartridge 12a is adjacent first side 20 of cartridge 12b; second side 22 of cartridge 12b is adjacent first side 20 of cartridge 12c; and second side 22 of cartridge 12c is adjacent first side 20 of cartridge 12d. In addition, cartridges 12a-12d are positioned on upper surface 46 of cover slip 44 such that first ends 16 of cartridges 12a-12d are axially aligned and such that second ends 18 of cartridges 12a-12d are axially aligned. Bracket 68 is deposited on upper surface 64 of substrate 54 such that flange 94 overlaps first side 20 of cartridge 12a, first ends 16 of cartridges 12a-12d, second side 22 of cartridge 12d, and second ends 18 of cartridges 12a-12d. In addition, outer surfaces of first and second side elements 70 and 72, respectively, of bracket 68 are substantially flush with corresponding first and second sides 56 and 58, respectively, of substrate 54 and the outer surfaces of first and second end elements 74 and 76, respectively, of bracket 68 are substantially flush with corresponding first and second ends 60 and 62, respectively, of substrate 54.

It is contemplated to mechanically clamp bracket 68 to substrate 54 so as to prevent leakage and cross channel contamination between channels 24a-24c along upper surface 46 of cover slip 44, but allow removal of bracket 68 from substrate 54. By way of example, screws, rivets, snap connectors or the like may extend through bracket 68 into substrate 54 so as to removably interconnect bracket 68 and substrate 54. Alternatively, a plurality of clamps 102 spaced about the outer periphery of bracket 68 may be used. Each clamp 102 includes upper arm 104 having a lower surface 106 engageable with upper surface 90 of bracket 68 and lower arm 108 having an upper surface 110 engageable with lower surface 66 of substrate 54. Biasing leg 112 interconnects upper and lower arms 104 and 108, respectively, and urges upper and lower arms 104 and 108, respectively, toward each other such that clamp 102 retains bracket 68 on substrate 54 and prevents leakage and cross channel contamination between channels 24a-24c along upper surface 46 of cover slip 44.

Once device 10 has been assembled, it can be appreciated that cells may be cultivated, fixated and stained on cover slip 44 utilizing each channel 24a-24c of each cartridge 12a-12d. Since multiple treatments may be performed on a single cover slip 44, less reagent can be used due, in part, to more efficient washing steps. In addition, the cells are provided in well defined and predictable locations 114a-114l on cover slip 44 with respect to fiduciary marks 45a-45d, FIG. 4.

In order image the cells on cover slip 44, clamps 102 are removed so as to disengage bracket 68 and substrate 54. Thereafter, bracket 68 and cartridges 12a-12d are removed from cover slip 44, FIG. 5. Cover slip 44 may then be removed from substrate 54 for mounting on glass slide 122 for imaging, FIG. 7. More specifically, lower surface 48 of cover slip 44 may be affix to upper surface 120 of glass slide 122. Imaging device 116, such as a microscope, may be brought into close proximity to upper surface 46 of cover slip 44 so as to allow a user to directly observe the treatments on cover slip 44. It can be appreciated that fiduciary marks 45a-45d facilitate the locating and auto-focusing of a treatment on cover slip 44. In addition, since multiple treatments are provided on a single cover slip 44, imaging of the other treatments merely require the simple x-y movement of imaging device 116.

Figure 5:
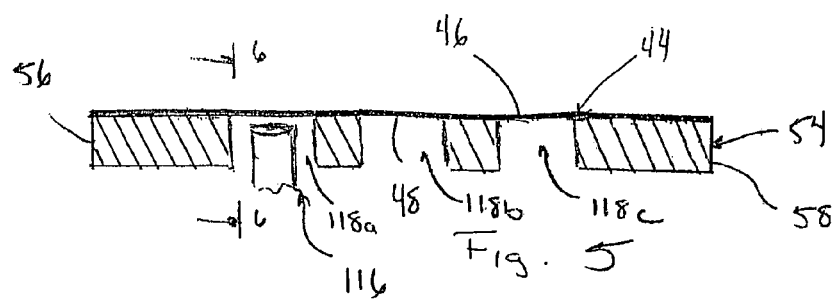
FIG. 5 is a cross sectional view of the substrate and cover slip taken along line 5-5 of FIG. 4.
Figure 6:
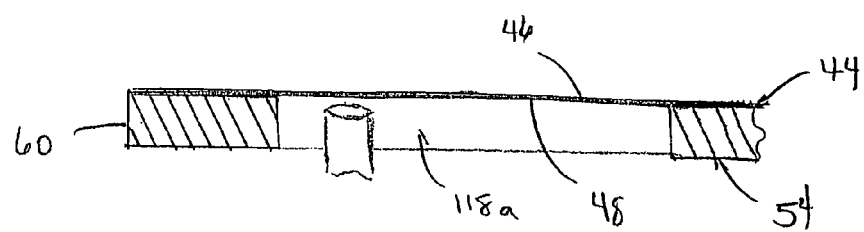
FIG. 6 is a cross-sectional view of the substrate and cover slip taken along line 6-6 of FIG. 5.

Alternatively, referring to FIGS. 5-6, it is contemplated to provide one or more openings 118a-118c through substrate 54 that are aligned with locations 114a-114l, heretofore described. As a result, imaging device 116, such as an inverted microscope, may be brought into close proximity to lower surface 48 of cover slip 44 so as to allow a user to directly observe the treatments on cover slip 44.

Various modes of carrying out the invention are contemplated as being within the scope of the following claims particularly pointing out and distinctly claiming the subject matter, which is regarded as the invention.

I claim:

1. A device for facilitating preparation of a sample for imaging, comprising:
    a cartridge having a generally flat, upper surface, a lower surface, an input port extending between the upper and lower surfaces thereof and an output port extending between the upper and lower surfaces thereof, the cartridge including a first recess in the lower surface thereof having a first end communicating with the input port, a second end communicating with the output port and a length therebetween;
    a cover slip having an upper surface engageable with the lower surface of the cartridge such that a portion of the upper surface of the cover slip communicates with the entirety of the length of first recess in the lower surface of the cartridge;
    a substrate having an upper surface positioned against the lower surface of the cover slip, a lower surface, a thickness between the upper and lower surfaces of the substrate and an oblong opening extending between the upper surface and the lower surface of the substrate and being in axial alignment with the first recess in the lower surface of the cartridge so as to overlap the portion of the cover slip, the opening:
        having a first end aligned the first end of the first recess and a second end aligned with the second end of the first recess; and
        being free of obstructions between the first and second ends thereof along the entire thickness of the substrate such that an image device is movable in the opening between a first position in alignment with the first end of the first recess and a second position in alignment with the second end of the first recess; and
    a removable connector selectively connectable to the cartridge and the substrate for removably connecting the cartridge to the substrate.

2. The device of claim 1 further comprising a bracket engageable with the cartridge on the substrate.

3. The device of claim 2 wherein the removable connector interconnects the bracket to the substrate for maintaining the cartridge on the substrate.

4. The device of claim 1 further comprising an adhesive for removably affixing the upper surface of the cover slip to the lower surface of the cartridge.

5. The device of claim 1 wherein the cartridge includes fiduciary marks.

6. The device of claim 1 wherein the cover slip includes fiduciary marks.

7. The device of claim 1 wherein the input port of the cartridge is defined by an input surface, at least a portion of the input surface being patterned to contain reagent droplets therein.

8. The device of claim 1 wherein the outlet port in the cartridge has a generally funnel shaped cross section.

9. A device for facilitating preparation of a sample for imaging, comprising:
- a cartridge having upper and lower surfaces and an elongated first recess in the lower surface thereof, the first recess having first and second opposite ends and a length therebetween;
- a cover slip having an upper surface engageable with the lower surface of the cartridge such that a first portion of the upper surface of the cover slip communicates with the entirety of the length of the first recess in the lower surface of the cartridge and a lower surface;
- a substrate having an upper surface positioned against the lower surface of the cover slip, a lower surface, a thickness between the upper and lower surfaces of the substrate and an oblong opening between the upper and lower surfaces of the substrate, the opening:
  - having a first end aligned the first end of the first recess and a second end aligned with the second end of the first recess; and
  - being free of obstructions between the first and second ends thereof along the entire thickness of the substrate such that an image device is movable in the opening between a first position in alignment with the first end of the first recess and a second position in alignment with the second end of the first recess; and
- a removable connector selectively connectable to the cartridge and the substrate for removably connecting the cartridge to the substrate.

10. The device of claim 9 wherein the lower surface of the cartridge includes a second recess therein, the upper surface of the cover slip having a second portion communicating with the second recess in the lower surface of the cartridge.

11. The device of claim 9 wherein the first and second recesses in the lower surface of the cartridge are generally parallel.

12. The device of claim 9 wherein the cartridge includes input and output ports, the input port being defined by a patterned input surface for containing reagent droplets therein and the outlet port having a generally funnel shaped cross section.

13. The device of claim 9 wherein the cartridge includes fiduciary marks.

14. The device of claim 9 wherein the cover slip includes fiduciary marks.

15. A device for facilitating preparation of a sample for imaging, comprising:
- a cartridge having upper and lower surfaces and a plurality of generally parallel recesses forming in the lower surface thereof, each recess having an input port at a first end thereof and an output port at a second end thereof;
- a cover slip having an upper surface engageable with the lower surface of the cartridge such that the upper surface of the cover slip and the plurality of recesses in the lower surface of the cartridge define a plurality of channels through the device;
- a substrate having an upper surface positioned against the lower surface of the cover slip, a lower surface, a thickness between the upper and lower surfaces of the substrate and a plurality of openings therethough, each opening:
  - being generally oblong and in axial alignment with a corresponding recess in the lower surface of the cartridge;
  - having a first end aligned the first end of the corresponding recess and a second end aligned with the second end of the corresponding recess; and
  - being free of obstructions between the first and second ends of the corresponding recess along the entire thickness of the substrate such that that an image device is movable in each opening between a first position in alignment with the first end of the corresponding recess and a second position in alignment with the second end of the corresponding recess; and
- a removable connector selectively connectable to the cartridge and the substrate for removably connecting the cartridge to the substrate.

16. The device of claim 15 wherein each input port is defined by a patterned input surface for containing reagent droplets therein.

17. The device of claim 15 wherein each outlet port has a generally funnel shaped cross section.

18. The device of claim 15 wherein the cartridge includes fiduciary marks.

19. The device of claim 15 wherein the cover slip includes fiduciary marks.

* * * * *